(12) United States Patent
Policappelli

(10) Patent No.: US 7,060,057 B2
(45) Date of Patent: Jun. 13, 2006

(54) COMFORTABLE TAMPON

(76) Inventor: Nini Policappelli, 361 N. Robertson Blvd., Los Angeles, CA (US) 90048

( * ) Notice: Subject to any disclaimer, the term of this patent is extended or adjusted under 35 U.S.C. 154(b) by 0 days.

(21) Appl. No.: 10/961,934

(22) Filed: Oct. 7, 2004

(65) Prior Publication Data

US 2005/0080393 A1    Apr. 14, 2005

Related U.S. Application Data

(63) Continuation-in-part of application No. 10/373,541, filed on Feb. 24, 2003, now abandoned.

(51) Int. Cl.
*A61F 13/15* (2006.01)
*A61F 13/20* (2006.01)

(52) U.S. Cl. ............... 604/385.12; 604/385.17; 604/385.18; 604/14

(58) Field of Classification Search ........... 604/385.12, 604/385.01, 385.17, 385.18, 904, 385.16, 604/11–18; D24/141
See application file for complete search history.

(56) References Cited

U.S. PATENT DOCUMENTS

| 4,230,686 | A | * | 10/1980 | Schopflin et al. | 424/425 |
| 4,787,895 | A | * | 11/1988 | Stokes et al. | 604/358 |
| 5,299,581 | A | * | 4/1994 | Donnell et al. | 128/830 |
| 2002/0095128 | A1 | * | 7/2002 | Petit | 604/385.18 |
| 2002/0177835 | A1 | * | 11/2002 | Zadini et al. | 604/385.12 |
| 2003/0153864 | A1 | * | 8/2003 | Chaffringeon | 604/15 |
| 2005/0113782 | A1 | * | 5/2005 | Carlin | 604/385.18 |
| 2005/0113787 | A1 | * | 5/2005 | Carlin | 604/385.18 |

FOREIGN PATENT DOCUMENTS

WO    WO 99/07433    *    2/1999

* cited by examiner

*Primary Examiner*—Jacqueline F. Stephens
(74) *Attorney, Agent, or Firm*—Trojan Law Offices

(57) ABSTRACT

A tampon comprising and elongated absorptive member, housing an elongated expandable member having a hollow cavity, which is expandable on insertion of air. Optionally, at least one non-absorptive member is arranged in a spaced relationship about the outside surface of the tampon material, the non-absorptive members causing a spacing between the absorptive member and vagina wall. This increases the comfort at the interface of the tampon with the vaginal walls.

20 Claims, 2 Drawing Sheets

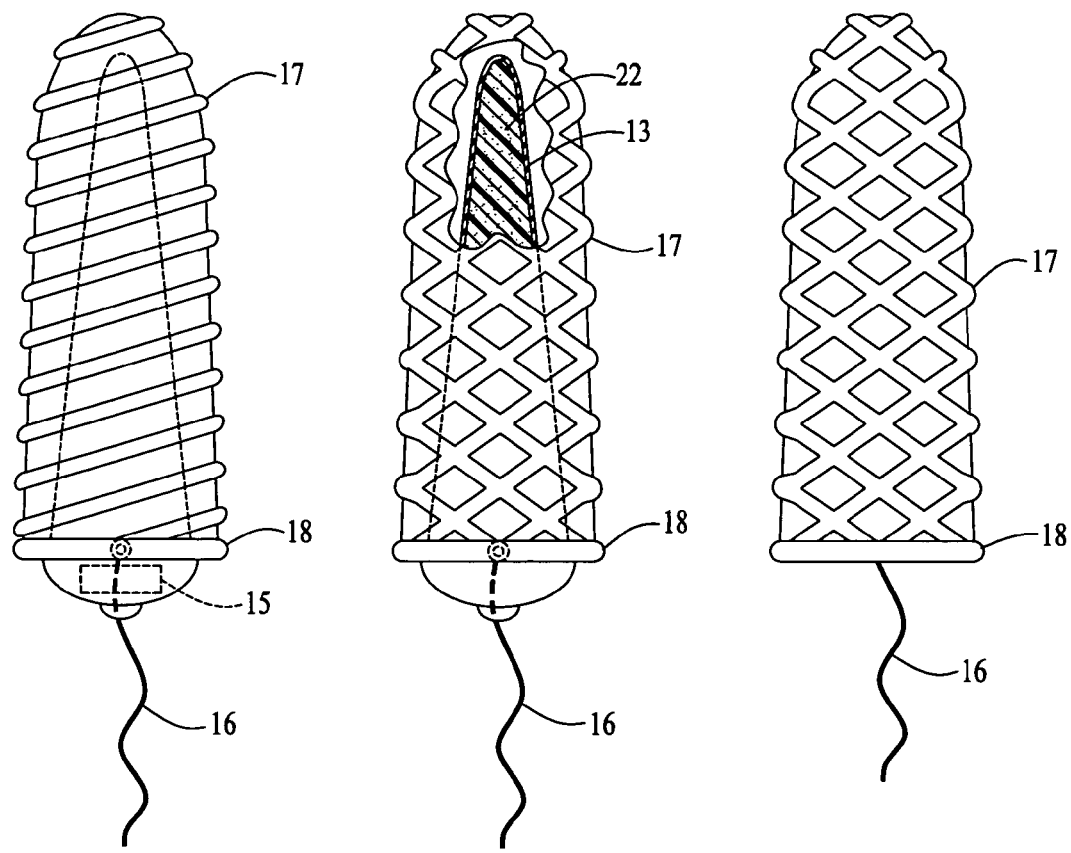

COMFORTABLE TAMPON

CLAIM OF PRIORITY

This application is a Continuation in Part of my application Ser. No. 10/373,541, filed on Feb. 24, 2003 now abandoned.

BACKGROUND OF THE INVENTION

1. Field of the Invention

The field of this invention relates to a tampon. In particular, the invention is concerned with a tampon that has improved comfort for the user.

2. Background

Vaginal tampons are commonly used to prevent the leakage of blood from a woman's vagina. A tampon is commonly made of a synthetic absorbent material such as cotton. A woman typically inserts a tampon into her vagina during the time of her menstrual period, during which menstrual blood flows toward and out of the opening of the vaginal canal. The absorbent material of the tampon is relied upon to absorb the menstrual blood, and to block the vaginal canal to a certain degree, thus preventing the leakage of the menstrual blood from the vaginal opening.

Many different forms and shapes of tampons are known. Generally, a tampon is shaped in such a way as to be insertable into the vaginal opening and slidable up the vaginal canal. Because of variety among the anatomy of women that use tampons worldwide, many women often experience discomfort when using tampons, which are typically all very similar in shape, texture, and size.

A female vagina has vaginal walls, which are normally coated with mucus, and which surround the vaginal canal. One of the functions of the mucus is to provide moisture to the vaginal canal. Vaginal dryness may occur when a tampon is kept in the vaginal canal for a prolonged period of time. Vaginal dryness may also occur when a more absorbent tampon is used than needed for the amount of a woman's menstrual flow. Vaginal dryness refers to the drying out of the mucus coating of the vaginal walls, causing dryness in the vaginal canal.

Removal of a tampon from a dry vaginal canal typically leaves behind a residue of synthetic pieces, which break off the absorptive portion of the tampon due to friction against the vaginal walls. The friction between the tampon and the dry vaginal walls can also tear cells off the vaginal wall and cause ulcerations in the lining of the vaginal walls.

Prolonged use of conventional tampons has been shown to have links to toxic shock syndrome, which is a condition that occurs when a certain type of bacteria enters the vaginal canal and releases toxins into the body. The bacteria causing this condition typically grow on the synthetic surface of the absorptive portion of the tampon.

Thus, a need exists for a tampon that has increased comfort for women when inside the vaginal canal, at the same time permitting effective absorption of bodily fluids in the absorptive portions of the tampon and reducing the area on which toxic shock syndrome-causing bacteria can grow.

SUMMARY OF THE INVENTION

According to the invention, there is provided a tampon for insertion into a vagina, which comprises an elongated absorptive member having an outside surface and a central axis. The tampon further comprises an elongated expandable member located within the elongated absorptive member. The expandable member is capable of expanding upon the entry of a fluid into the expandable member.

The tampon further comprises at least one non-absorptive member spatially positioned about the outside surface of the elongated absorptive member. The expansion of the expandable member causes the absorptive member and the non-absorptive members to be edged outwardly from the central axis into a relatively closer engagement with walls of the vagina.

The non-absorptive members are spaced on the outside surface of the absorptive member and protrude outwardly from the surface of the absorptive member. The orientation of the non-absorptive members effectively permits the walls of the vagina, which would otherwise normally be in contact with the absorptive member, to only have an interaction with the non-absorptive members. This design provides an improved comfort field of the tampon in the vagina, as it eliminates the friction of the absorptive member, typically cotton, against the walls of the vaginal canal.

The non-absorptive members can be in the form of a spiral, shaped around the outside surface of the absorptive member. The non-absorptive member can also be in the form of a sleeve positioned over the absorptive area of the tampon. One non-absorptive member may be in the form of a rim and is typically located near the end of the tampon that is proximal to the vaginal opening. This rim is expandable and when it comes in contact with the vaginal walls, it provides a sealing effect in the vaginal canal.

The non-absorptive members are typically formed of suitable pharmaceutical grade silicone and may be lubricated as necessary. The silicone material is elastic and stretchable. The silicone may be optionally impregnated or coated with at least one pharmaceutical agent. When such tampon is inserted into a woman's vagina, the pharmaceutical agent will absorb into the woman's body from the silicone surface.

In a preferred form of the invention, the expandable member is centrally located and contains a canister containing a pressurized medium, usually a fluid. Typically, the fluid used is carbon dioxide, but any other medium, including air, can be used. A string is connected to the container so that the pulling of the string releases the fluid from the canister into the cavity of the expandable member.

In a further preferred form of the invention, the expandable member includes a valve, which acts as airflow control between the inside and the outside of the expandable member's hollow cavity. The tampon also includes a pump, connected to the valve, for injection of fluid into the elongated area. The valve can permit fluid to pass into the hollow cavity of the expandable member and can be selected to permit fluid to exit from the cavity. In this form of the invention, the fluid is air and the pump acts to permit air to pass into the cavity in the first mode of operation. In the second mode of operation, the valve permits the air to exit the cavity.

In yet another preferred form of the invention, the expandable member is vacuum packed and may be at least partly filled with a resin or a sponge material. In use, the user opens the vacuum package, and the expandable member expands due to the influx of a combination air and bodily fluids. The expansion of the expandable member is promoted when the resin or sponge material stored inside of the expandable member comes in contact with and absorbs a bodily fluid.

In yet a further preferred embodiment of the invention, no expandable member is housed within the absorptive member. The tampon comprises just the absorptive member and at least one non-absorptive member. Because the elongated absorptive member is typically manufactured from cotton, the absorptive member naturally expands upon cotton's absorption of a bodily fluid such as blood. In this embodiment, the expansion of the absorptive member causes the non-absorptive member to be edged outwardly from the central axis into a relatively closer engagement with walls of the vagina.

The tampon also comprises a cord for facilitating the withdrawal of the tampon from the vaginal canal. In one preferred embodiment, this cord is also connected to the pressurized medium canister and is used to facilitate the release of the medium into the expandable member. In another preferred embodiment, this string is also connected to the pump and is used to initiate the injection of a medium into the expandable member.

BRIEF DESCRIPTION OF THE DRAWINGS

FIG. 4 is a side view of an alternate design of the invention.

FIG. 5 is a side view of another alternate design.

FIG. 6 is a side view of yet another alternate design.

DETAILED DESCRIPTION OF THE PREFERRED EMBODIMENTS

Figures 1, 2, 3:
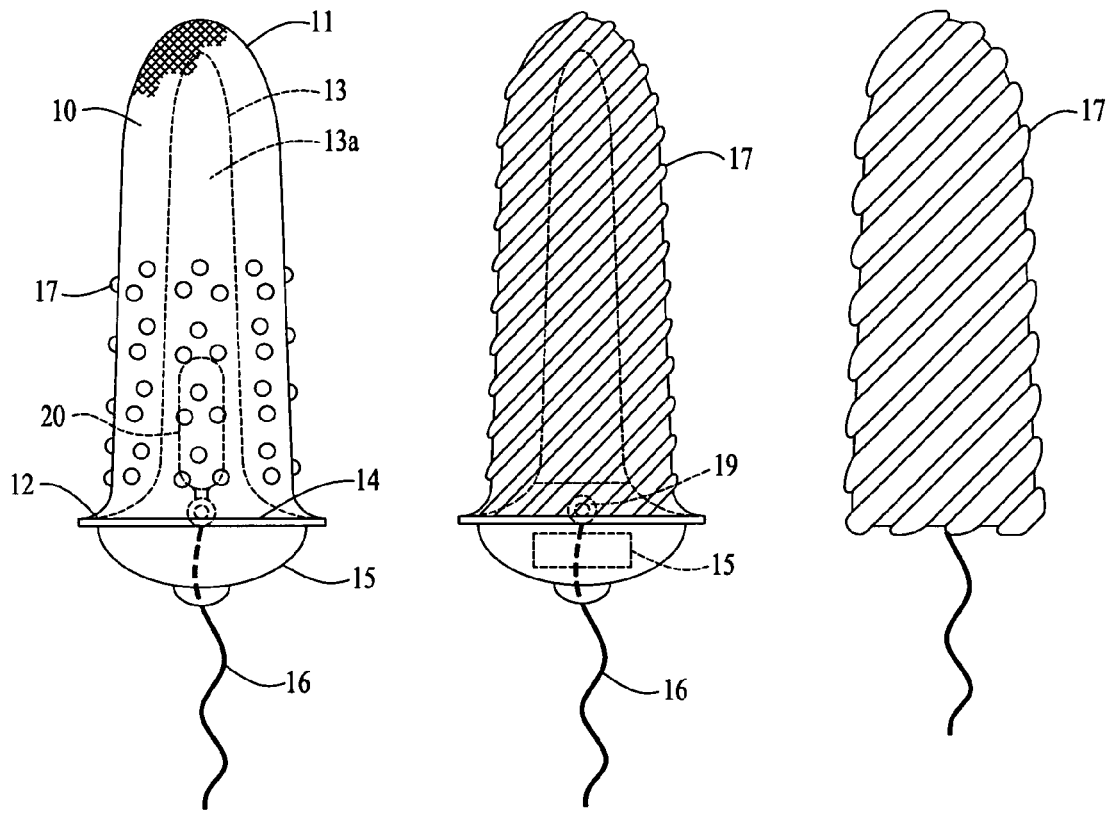
FIG. 1 is a side view of the preferred embodiment of the invention.
FIG. 2 is a cross-sectional view of another embodiment of the invention.
FIG. 3 is a side view of another embodiment of the invention.

In the following description of the preferred embodiments reference is made to the accompanying drawings, which form the part thereof, and in which are shown by way of illustration of specific embodiments in which the invention may be practiced. It is to be understood that other embodiments may be utilized and structural and functional changes may be made without departing from the scope of the present invention.

A tampon includes an elongated absorptive member 10. The absorptive member 10 is typically made of one or more layers of absorptive material such as cotton, or other absorptive synthetic materials. The lead end 11 of the tampon is for insertion into the vagina and the trailing end 12 is located proximal to the mouth of the vagina. A string or cord 16 is attached to the trailing end 12. Pulling of the string 16 facilitates the withdrawal of the tampon from the vagina.

In all of the embodiments described below, the outside surface of the absorptive member 10 includes at least one lubricated non-absorptive member 17. The non-absorptive members 17 are arranged in a spaced relationship about the outside surface of the absorptive member 10. The non-absorptive members 17 protrude generally outwardly from the surface of the absorptive member 10.

Because they protrude outwardly from the outside surface of the absorptive member 10, the non-absorptive members 17 prevent the vaginal walls from direct contact with the cotton of the absorptive member 10, since the cotton is located underneath and between the silicone of the non-absorptive members 17. The non-absorptive members 17 improve the comfort level of the user when the tampon is located in the vagina because they prevent friction between the outside surface of the absorptive member 10 and the vaginal walls (not shown). The non-absorptive members 17 also prevent scratching and lacerations of the vaginal wall caused by the friction of a typical tampon and the vaginal wall, when the tampon is being taken out of the vagina.

The user may fit the non-absorptive members 17 onto the tampon before inserting the tampon into the vagina. As such, the non-absorptive member 17 can be a sleeve, which is fitted over the absorptive member 10. The tampon is typically manufactured with pharmaceutical grade elastic expandable silicone material, which is suitably embedded or formed on the outside surface of the absorptive member 10 in a manner that is securely anchored so that its inadvertent release or separation from the tampon is not possible.

As shown in FIG. 1, the non-absorptive members 17 can be individually spaced on the outside surface of the absorptive member 10. In FIG. 2, the non-absorptive members 17 can form a spiral about the outside of the absorptive material. In FIG. 3 the non-absorptive members 17 form a spiral about the outside surface of the absorptive member 10, and in this configuration of the tampon, there is no elongated expandable member 13 within the non-absorptive member 10.

As shown in FIGS. 4, 5, and 6, at least one non-absorptive member 18 may be in the form of a rim and is typically located in proximity to the trailing end 12 of the tampon. This non-absorptive member 18 is expandable and when it comes in contact with the vaginal walls, it provides a sealing effect in the vaginal canal.

In FIG. 4 the spiraling non-absorptive members 17 are shown with a different angular relationship to the absorptive materials of the tampon. This configuration uses a pump 15. In FIG. 5, the elongated expandable member 13 is shown vacuum packed with a sponge material 22, and a meshed arrangement of the non-absorptive members 17 is shown. In FIG. 6 there is a similar meshed arrangement of non-absorptive members 17, but without a pump 15.

The silicone of the non-absorptive member 10 may be optionally impregnated or coated with a pharmaceutical agent (not shown). When the tampon is inserted into the vagina, the pharmaceutical agent is absorbed into the woman's body from the silicone surface of the non-absorptive member 10. This use of the tampon can treat certain infections or other medical conditions of the user.

In the preferred embodiment of the invention, an elongated expandable member 13 is located within the absorptive member 10. The elongated expandable member 13 contains a hollow cavity 13A, which contains a canister 20 filled with a pressurized medium. The pressurized medium typically used is carbon dioxide, but any other medium, including air, can be used. The canister 20 is connected to string 16. When string 16 is pulled by a user to a pre-determined setting, the canister 20 is caused to release its contents into the elongated expandable member 13. The string 16 can be made out of elastic or non-elastic material.

In another preferred embodiment of the invention, the absorptive member 10 also contains the elongated expandable member 13. The elongated expandable member 13 contains a hollow cavity 13A and a valve 19. The valve 19 acts as airflow control between the hollow cavity 13A of the expandable member 13 and the outside environment. The trailing end of the tampon 12 contains a pump 15, which can inject a medium into the hollow cavity 13A of the expandable member 13 through the valve 19. The pump is typically activated by pulling the string 16 to a pre-determined setting. The medium used is typically air. The hollow cavity 13A of the expandable member 13 and the pump 15 form a selectively closed chamber. In one mode of operation, the valve only allows air to enter the hollow cavity 13A of the expandable member 13. Under appropriate circumstances, the valve 19 can operate in the reverse direction to permit air to be withdrawn from the hollow cavity 13A.

In yet another preferred form of the invention, the expandable member 13 is vacuum packed and may be at least partly filled with a resin or a sponge material 22. In use, the user opens the vacuum package, and the expandable member 13 expands due to the influx of air and bodily fluids. Typically, the user opens the vacuum package by pulling string 16 to a pre-determined setting. The expansion of the expandable member 13 is promoted when the resin or sponge material 22 stored inside of the expandable member 13 comes in contact with and absorbs a bodily fluid.

In yet another preferred embodiment of the invention, the elongated absorptive member 10 does not house an expandable member 13 inside of it. Since the absorptive member 10 is typically made out of cotton-like material, the absorptive member 10 naturally expands when the cotton absorbs a bodily fluid, typically blood. The expansion of the absorptive member 10 causes the non-absorptive member 13 to be edged outwardly from the central axis into a relatively closer engagement with walls of the vagina.

The non-absorptive members 17, since they are made out of silicone, provide a sealing effect for the vaginal canal when they move into contact with the walls of the vagina. This enhances the ability of the tampon to prevent the unwanted leakage of menstrual blood from the vagina.

Since the surface of the silicone is smooth, when compared to cotton, the interaction between the silicone and the vaginal walls is more comfortable for the user. Finally, since the silicone protrudes over the surface of the absorptive member 10, when the tampon is taken out from the vaginal canal, the friction between the absorptive member 10 and the vaginal walls is eliminated. This prevents residual pieces of cotton from being left on the vaginal walls and prevents unwanted irritation of the vaginal walls.

The tampon of the current invention improves comfort, reduces the chances of vaginal infection and toxic shock syndrome and its use minimizes the irritation and damage to the vaginal walls.

Many modifications and variations are possible in light of the above teaching. The foregoing is a description of the preferred embodiments of the invention and has been presented for the purpose of illustration and description. It is not intended to be exhaustive and so limit the invention to the precise form disclosed.

The invention is to be determined by the following claims:

1. A tampon for insertion in a vagina comprising:
   an elongated absorptive member having an outside surface and a central axis;
   at least one expandable member within said absorptive member, said expandable member having a hollow cavity, said hollow cavity containing a canister, said canister capable of storing and releasing a medium into said hollow cavity;
   at least one non-absorptive member arranged in a spaced relationship about the outside surface of said elongated absorptive member, said at least one non-absorptive member protruding outwardly from said surface of the absorptive member;
   wherein upon release of a medium from said canister into said cavity, the expandable member expands, thereby urging the absorptive member and the non-absorptive member generally outwardly from the central axis and into a closer engagement with a wall of the vagina, and
   wherein the outside surface of the absorptive member is prevented from direct contact with the wall of the vagina by said at least one non-absorptive member.

2. The tampon of claim 1, further comprising a string, wherein the pulling of said string is capable of withdrawing the tampon from the vagina.

3. The tampon of claim 2, wherein pulling said string to a predetermined setting causes said canister to release the medium into said hollow cavity.

4. The tampon of claim 1, wherein said non-absorptive member is made out of silicone.

5. The tampon of claim 4, wherein said silicone is impregnated with a pharmaceutical agent, said pharmaceutical agent capable of being absorbed into a woman's body upon insertion of said tampon into the vagina.

6. The tampon of claim 1, wherein the medium is carbon dioxide.

7. A tampon for insertion in a vagina comprising:
   an elongated absorptive member having an outside surface and a central axis, said absorptive member being made out of material capable of expanding upon absorbing a bodily fluid;
   at least one non-absorptive member arranged in a spaced relationship about substantially the entire outside surface of said elongated absorptive member, said at least one non-absorptive member protruding outwardly from said surface of the absorptive member;
   wherein the absorptive member expands upon absorbing a bodily fluid, thereby urging the absorptive member and the non-absorptive member to move generally outwardly from the central axis and into a closer engagement with a wall of the vagina, and
   wherein substantially the entire outside surface of the absorptive member is prevented from direct contact with the wall of the vagina by said at least one non-absorptive member.

8. The tampon of claim 7, further comprising a string, wherein pulling said string withdraws the tampon from the vagina.

9. The tampon of claim 7, wherein said non-absorptive member is made out of silicone.

10. The tampon of claim 9, wherein said silicone is impregnated with a pharmaceutical agent, said pharmaceutical agent capable of being absorbed into a woman's body upon insertion of said tampon into the vagina.

11. A tampon for insertion in a vagina comprising:
    an elongated absorptive member having an outside surface and a central axis;
    at least one expandable member within said absorptive member, said expandable member having a hollow cavity, said hollow cavity containing a valve capable of allowing a medium to enter said cavity;
    at least one non-absorptive member arranged in a spaced relationship about substantially the entire outside surface of said elongated absorptive member, said at least one non-absorptive member protruding outwardly from said surface of the absorptive member;
    wherein upon entry of a medium into said cavity, the expandable member expands, thereby urging the absorptive member and the non-absorptive member generally outwardly from the central axis and into a closer engagement with a wall of the vagina; and
    wherein substantially the entire outside surface of the absorptive member is prevented from direct contact with the wall of the vagina by said at least one non-absorptive member.

12. The tampon of claim 11, further comprising a pump for urging a medium into said hollow cavity.

13. The tampon of claim 11, wherein said elongated member is vacuum packed.

14. The tampon of claim 13, wherein said elongated member is at least partly filled with material and wherein said material is capable of expanding.

15. The tampon of claim 11, wherein said valve is capable of allowing a medium to exit said hollow cavity.

16. The tampon of claim 11, further comprising a string, wherein the pulling of said string is capable of withdrawing the tampon from the vagina.

17. The tampon of claim 16, wherein pulling said string to a predetermined setting causes said pump to urge a medium into said hollow cavity.

18. The tampon of claim 11, wherein said non-absorptive member is made out of silicone.

19. The tampon of claim 18, wherein said silicone is impregnated with a pharmaceutical agent, said pharmaceutical agent capable of being absorbed into a woman's body upon insertion of said tampon into the vagina.

20. The tampon of claim 11, wherein said medium is air.

* * * * *